(12) United States Patent
Choung (10) Patent No.: US 6,332,778 B1
(45) Date of Patent: Dec. 25, 2001

(54) IMMEDIATELY LOADABLE EXPANDING IMPLANT

(75) Inventor: Pill-Hoon Choung, Seoul (KR)

(73) Assignee: Pill-Hoon Jung, Seoul (KR)

( * ) Notice: Subject to any disclaimer, the term of this patent is extended or adjusted under 35 U.S.C. 154(b) by 0 days.

(21) Appl. No.: 09/503,242

(22) Filed: Feb. 14, 2000

(30) Foreign Application Priority Data

Feb. 12, 1999 (KR) .................................................. 99/5167

(51) Int. Cl.$^7$ ............................................................ A61C 8/00
(52) U.S. Cl. ................................................ 433/173; 433/172
(58) Field of Search ...................................... 433/172, 173, 433/174, 175, 176

(56) References Cited

U.S. PATENT DOCUMENTS

| | | | | |
|---|---|---|---|---|
| 2,721,387 | * | 10/1955 | Ashuckian | 433/173 |
| 3,579,831 | * | 5/1971 | Stevens | 433/174 |
| 4,177,562 | * | 12/1979 | Miller et al. | 433/174 |
| 5,762,500 | * | 6/1998 | Lazarof | 433/173 |
| 6,126,662 | * | 10/2000 | Carmichael | 433/173 |

* cited by examiner

*Primary Examiner*—John J. Wilson
(74) *Attorney, Agent, or Firm*—Robert E. Bushnell, Esq.

(57) ABSTRACT

An implant provided with a fixture which is fixedly inserted into a socket and an abutment which is coupled to an upper portion of the fixture, characterized in that the fixture comprises a hollow fixture body which a plurality of screw threads are repeatedly formed along the circumference of the outer face thereof, and a partition wall formed with a through hole is integrally formed in an inside wall thereof and divides the inner space of the fixture body into an upper abutment receiving portion and a lower nut receiving portion, and which is formed with at least one slot extended from a lower end of the fixture body to a first position, a screw of which a head portion is caught by the partition wall and positioned at the abutment receiving portion and a body portion is extended through the through hole to a lower portion of the nut receiving portion, and a nut which is fitted to the body potion of the screw and moved upward and downward in the nut receiving portion by the rotation of the screw; wherein the nut receiving portion is formed so that the fixture body begins to be outwardly expanded when the nut is moved to the first position.

19 Claims, 8 Drawing Sheets

IMMEDIATELY LOADABLE EXPANDING IMPLANT

CLAIM OF PRIORITY

This application makes reference to, incorporates the same herein, and claims all benefits accruing under 35 U.S.C. §119 from an application for IMMEDIATELY LOADABLE EXPANDING IMPLANT earlier filed in the Korean Industrial Property Office on Feb. 12, 1999 and there duly assigned Serial No. 5167/1999.

BACKGROUND OF THE INVENTION

1. Field of the Invention

The present invention relates to an implant, more particularly, an immediately loadable expanding implant which is adapted to various shapes and sizes of a socket formed in a jawbone, from which a tooth has just been extracted, and comprised of a fixture which is inserted and then expanded in the socket and an abutment which is coupled to an upper portion of the fixture.

2. Description of the Related Art

An implant fixture, which is inserted into a socket of an extracted tooth and serves as the tooth, has been developed to various different forms. Recently, a screw type implant fixture is widely used.

However, this screw type implant fixture should be immediately inserted into a socket, after the tooth is extracted. In case that a width of the gum is narrow, there is a problem of fixing the screw type implant fixture. That is, when the implant fixture is immediately inserted into the socket, after the tooth is extracted, it is not easy to fix the implant fixture into the socket because the implant fixture is smaller than an upper portion of the socket of the extracted tooth and has a different structure from a shape of the extracted tooth. In other words, for example, a front tooth or premolar has a structure in which a right-left width size is larger than a front-back width size. And the tooth generally has two or three roots. However, the screw type implant fixture does not reflect these points. Further, in case that the width of the gum is narrow or an inside diameter of the socket is reduced by the expansion of the gum, there is a problem that a part of the screw is exposed from the implant fixture.

In addition, the abutment coupled to the upper portion of the implant fixture is fixed to the implant fixture by a locking screw. However, the operation for fixing a tooth is very complicate.

Moreover, if saliva is permeated through a cap between the implant fixture and the abutment, there are some fears of being infected with a germ contained in the saliva or shaking of the fixture.

SUMMARY OF THE INVENTION

It is therefore an object of the present invention to provide an implant in which a lower portion of the implant corresponding to the tooth root is expanded and fastened on an inside wall of a jawbone in the socket.

It is other object of the present invention to provide an expanding implant which is adapted to various shapes and sizes of a socket formed in the jawbone.

It is another object of the present invention to provide an implant in which the abutment is facilely coupled to the fixture.

It is yet another object of the present invention to provide an implant which prevents the saliva from permeating through a cap between the implant fixture and the abutment, thereby preventing from being infected with a germ contained in the saliva.

To achieve the above objects and other advantages, there is provided an implant provided with a fixture inserted into a socket and an abutment coupled to an upper portion of the fixture. The fixture includes a hollow fixture body, a plurality of screw threads repeatedly formed along a circumferential outer face thereof, and a partition wall having a through hole. The partition wall integrally formed in an inside wall thereof and divides the inner space of the fixture body into an upper abutment receiving portion and a lower nut receiving portion. The fixture is formed with at least one slot extended from a lower end of the fixture body to a first position. The fixture includes a screw of which a head portion rests against the partition wall and positioned at the abutment receiving portion and of which a body portion is extended through the through hole to a lower portion of the nut receiving portion. A nut is fitted to the body potion of the screw and moved upward and downward in the nut receiving portion by the rotation of the screw. The nut receiving portion is formed so that the fixture body begins to be outwardly expanded when the nut is moved to the first position.

The nut comprises a nut body which is formed with a through hole extended from an upper end to a lower end and has various shapes corresponding to the socket, and a guiding body which is outwardly projected from an upper portion of the nut body and is inserted into the slot, and wherein the body of the nut has a shape corresponding a shape of the inside wall of the fixture body from the upper end of the nut receiving portion to the first position.

Further, the partition wall has a ring-shaped protrusion on an upper portion thereof which is at the side of the abutment receiving portion, the screw has a ring-shaped groove corresponding to the protrusion.

Preferably, the fixture further comprises a cap which is coupled to the lower end of the fixture body, and the cap has a hemisphere shape having a receiving groove for receiving the lower end of the fixture body, and the cap is formed with a thread on an inside wall of the receiving groove.

Preferably, the fixture body is integrally formed with a neck portion on the upper portion thereof, the neck portion is formed with a thread to coupled to the abutment.

Preferably, the abutment is integrally formed with the fixture body.

Further, according to the present invention, there is provided an implant provided with a fixture which is fixedly inserted into a socket and an abutnent which is coupled to an upper portion of the fixture. The fixture comprises a hollow fixture body, a plurality of screw threads formed along the circumference of the outer face thereof, and a partition wall formed with a through hole, integrally formed in an inside wall thereof, and dividing the inner space of the fixture body into an upper abutment receiving portion and a lower nut receiving portion. The fixture includes at least one slot extended from a lower end of the fixture body to a first position, a screw of which a head portion rests on the partition wall and positioned at the abutment receiving portion and of which a body portion is extended through the through hole to a lower portion of the nut receiving portion, and a nut which comprises a nut body and a guiding protrusion, the nut having various cross-sections corresponding to a shape of the socket and having a through hole, and the guiding protrusion being outwardly projected from its upper end and being inserted into the slit, fitted to the body portion of the screw, and moved upward and downward by a rotation of the screw, wherein an inside wall of the nut receiving portion entirely has a parabola shape having a first position as a peak point, when the nut is moved from an upper end of the nut receiving portion to the first position, the fixture body begins to be outwardly expanded.

Preferably, the fixture body has an expanding rate and an expanding portion which is varied according to a shape and form of the parabola.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawings in which like reference symbols indicate the same or similar components, wherein.

DETAILED DESCRIPTION OF THE PREFERRED EMBODIMENTS

The present invention now will be described more fully hereinafter with reference to the accompanying drawings, in which preferred embodiments of the invention are shown.

Figure 1:
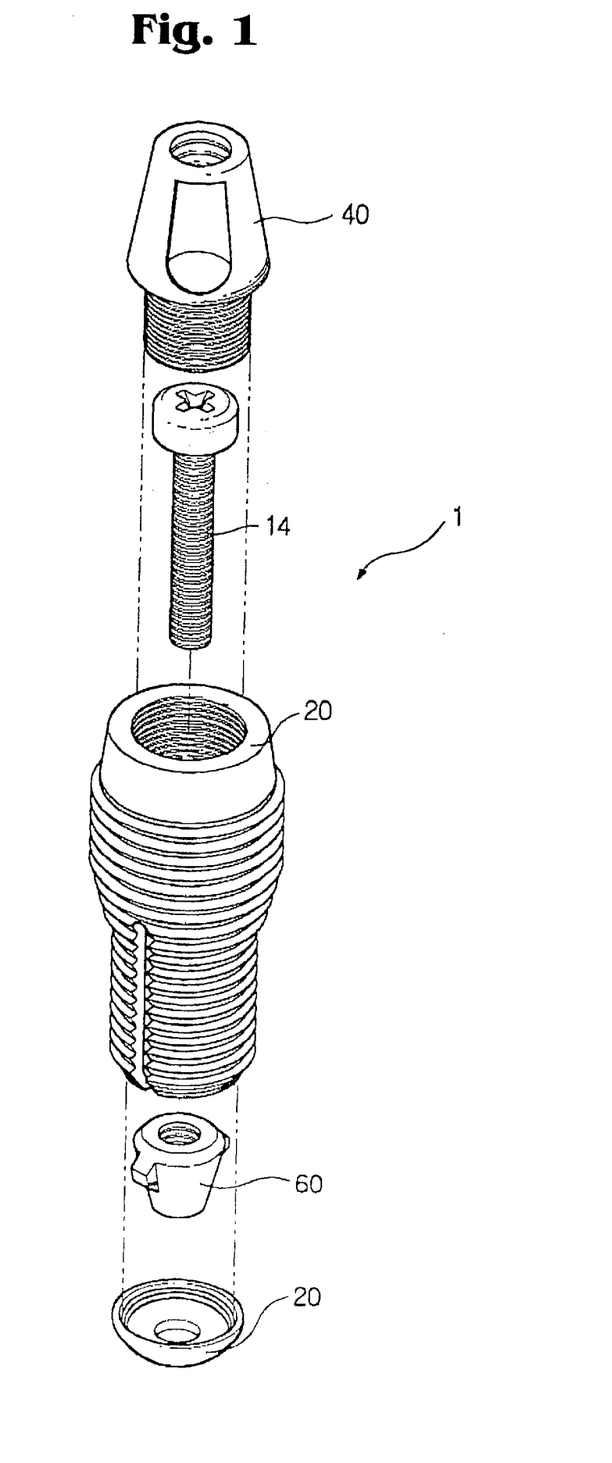
FIG. 1 is an exploded perspective view of a split type implant according to one embodiment of the present invention.
Figure 2:
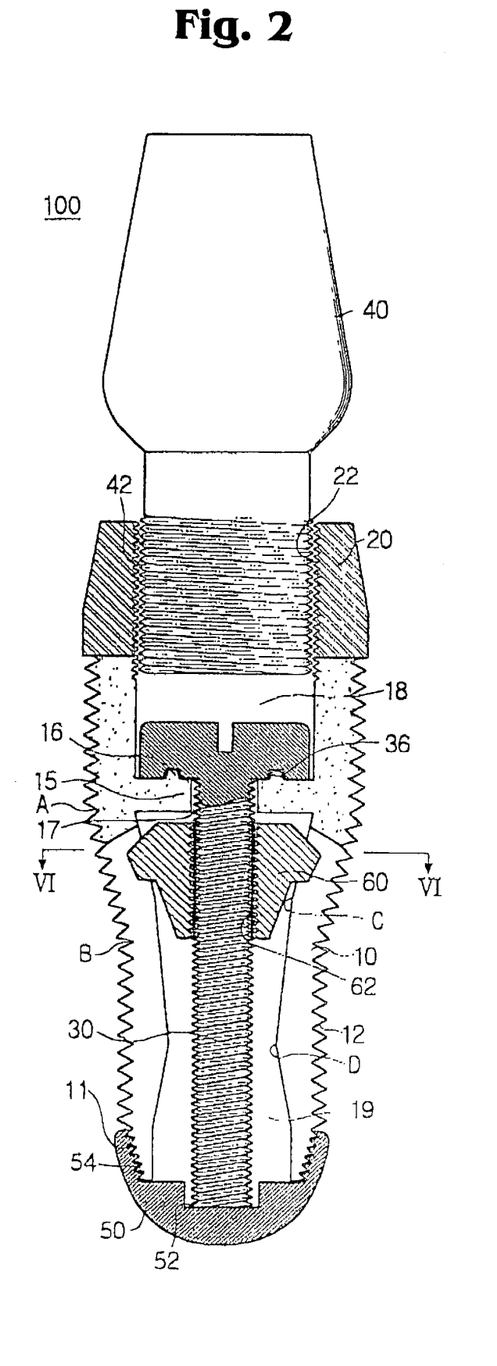
FIGS. 2 and 3 are cross-sectional views of the split type implant in FIG. 1.
Figure 3:
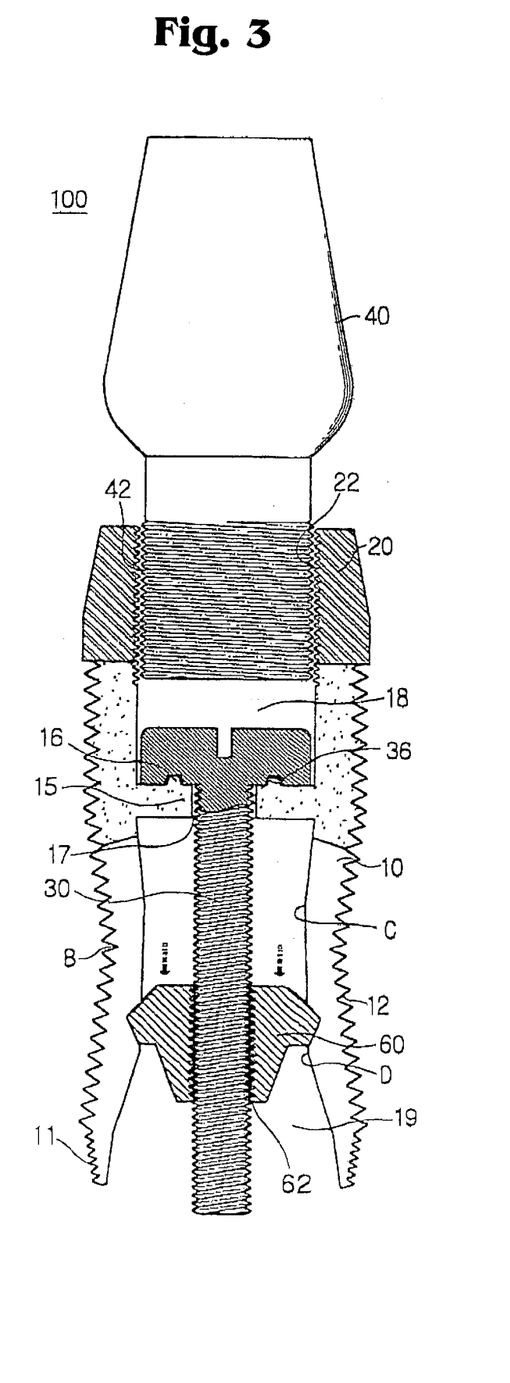

Referring to FIGS. 1 to 3, an implant 100 is comprised of a fixture 1 and an abutment 40 which is coupled to the fixture 1.

The fixture 1 comprises a fixture body 10, a neck portion 20 which is integrally formed on an upper portion of the fixture body 10 and a cap 50 which is selectively coupled to a lower portion of the fixture body 10.

It is preferred that the fixture body 10 is entirely formed into a tooth shape. For example, the fixture body 10 is firstly bent at a point A so that the outside diameter of the fixture body 10 is gradually reduced, and secondly bent at a point B. Then, the outside diameter of the fixture body 10 is continuously sustained until its lower end. Of cause, the fixture body 10 may has a constant outside diameter from the upper end to the lower end, regardless of the tooth shape. However, the stepped form of the fixture body 10 is advantageous in inserting the fixture body 10 into a socket from which a tooth is extracted. In addition, on the entire outer face of the fixture body 10 except the neck portion 20, a plurality of screw threads are repeatedly formed along the circumference of the outer face of the fixture body 10. Therefore, as described below more fully, the contact area between the inside wall of the socket and the outer face of the fixture body 10 is increased so that the fixture body 10 is fixedly mounted on the inside wall of the socket. Further, the screw thread may be changed into various different shapes.

On the outer face of the lower end of the fixture body 10, there is also formed a thread portion 11. A cap 50 is mounted on the thread portion 11.

Figure 6A:
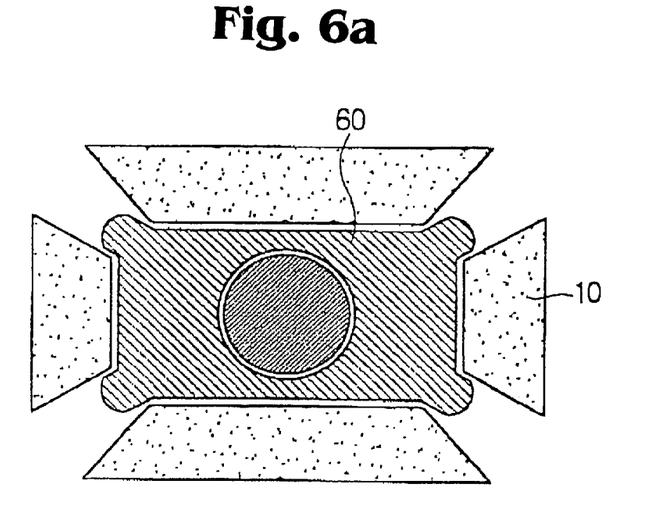
FIGS. 6A to 6E are cross-sectional views showing various kinds of nuts employed in the present invention.
Figure 6B:
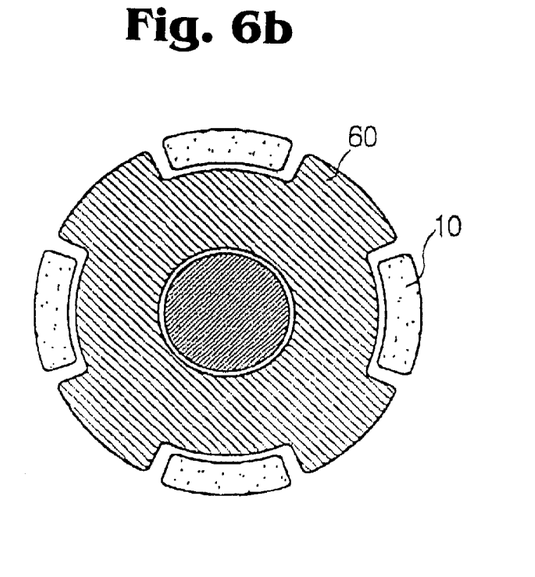
Figure 6C:
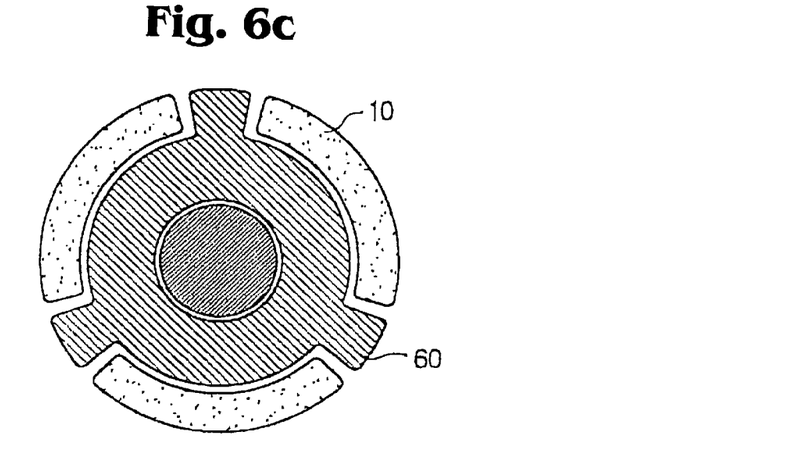
Figure 6D:
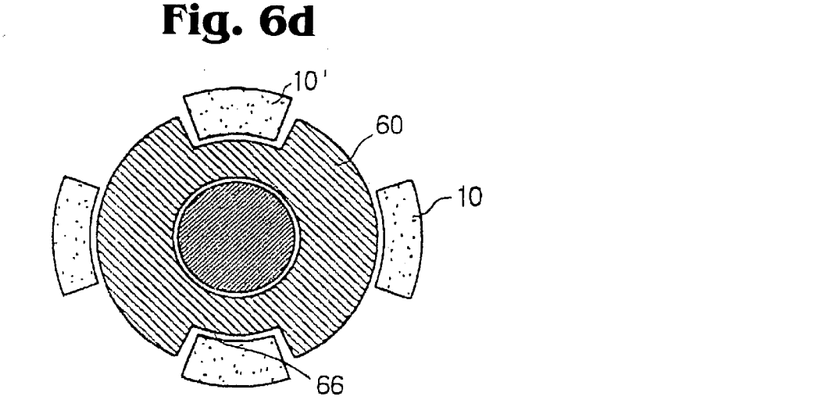
Figure 6E:
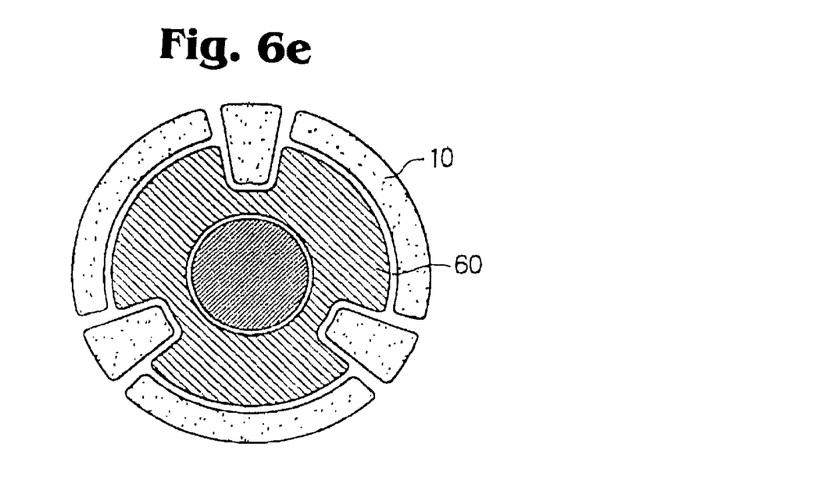

Meanwhile, the fixture body 10 may have various cross-sectional shape corresponding to the forms of the socket and the jawbone, as shown in FIGS. 6A to 6C. That is, the fixture body 10 is formed into various shapes, e.g. a circle type, an ellipse type, or a quadrangle type so as to be adapted to various structures of the socket and the jawbone. Further, the size of the fixture body 10 may be also varied. In this embodiment, the fixture body 10 has a constant thickness. However, if necessary, the thickness of the fixture body 10 may be varied, as shown in FIGS. 6D and 6E.

The fixture body 10 is a hollow pillar. At an inner meddle portion for the hollow fixture body 10, there is integrally formed a partition wall 15 which is formed with a through hole 17 at a center portion thereof. The partition wall 15 divides the inner space of the fixture body 10 into an upper abutment receiving portion 18 and a lower nut receiving portion 19.

Figure 7A:
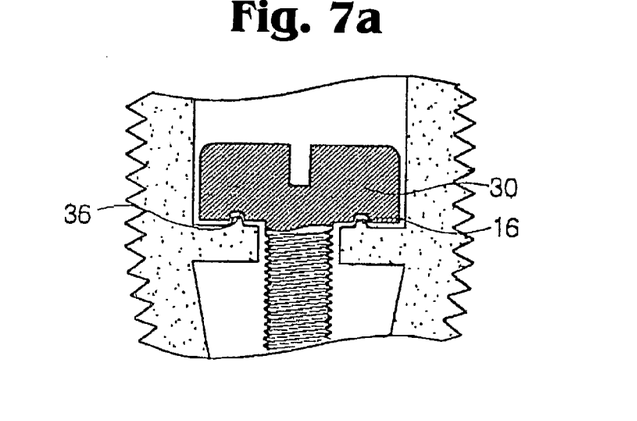
FIGS. 7A to 7F are cross-sectional views showing various kinds of means for preventing the permeation of saliva.
Figure 7B:
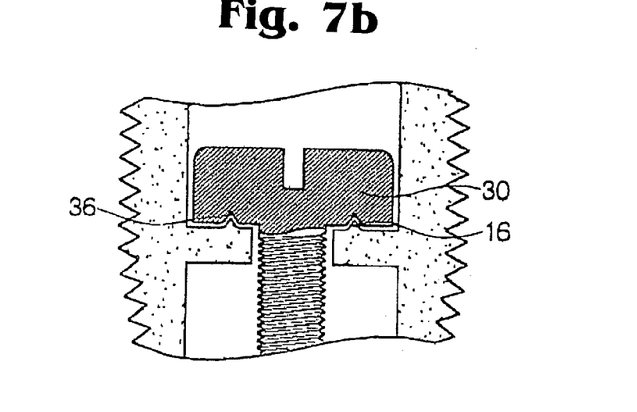
Figure 7C:
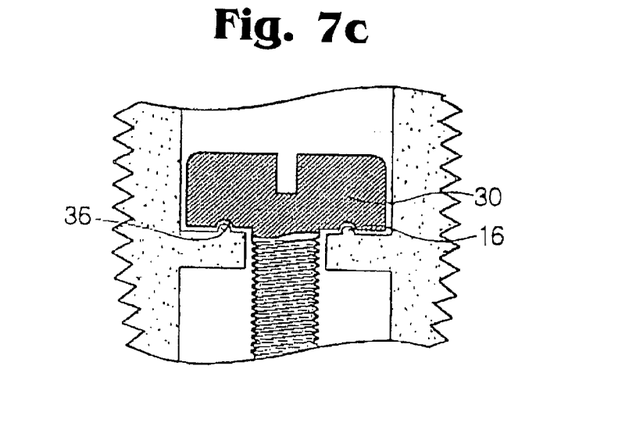
Figure 7D:
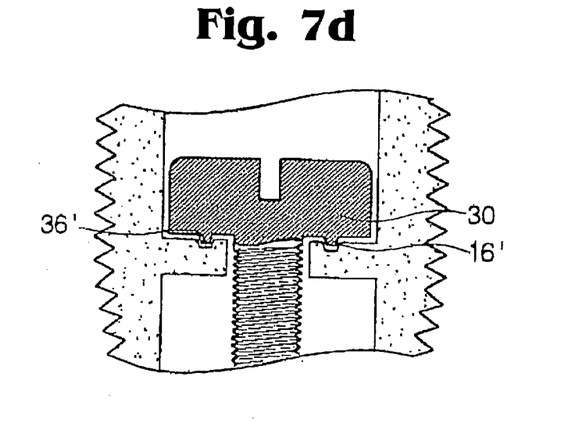
Figure 7E:
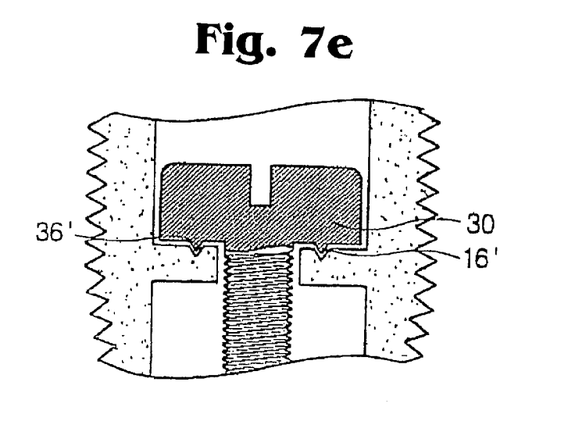
Figure 7F:
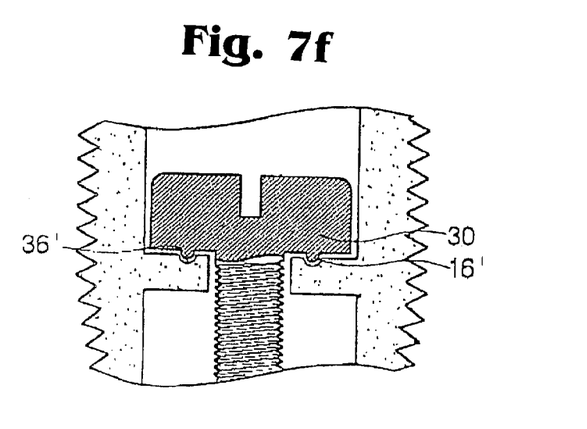

On the inside wall of the abutment receiving portion 18, there is provided a female screw 22 having a desired height from the upper end portion of the abutment receiving portion 18 to a desired depth so that the abutment is screwed into the thread 22. In addition, a screw 30 is inserted into the through hole 17. A head portion of the screw 30 is caught by the partition wall 15. The rest body portion of the screw 30 is positioned in the nut receiving portion 19. At this time, a ring-shaped protrusion 16 is formed on an upper face of the partition wall 15. On a bottom face of the head portion of the screw 30 corresponding to the ring-shaped protrusion 16, there is provided a groove 36. Referring to FIGS. 7A to 7C, the ring-shaped protrusion 16 may have various kinds of cross-sections, e.g. a trapezoid, a triangle or a circle type. Further, conversely, the head portion of the screw 30 may have a ring-shaped protrusion 16', and a groove 36' may be formed on the partition wall 15 corresponding to the ring-shaped protrusion 16', as shown in FIGS. 7D to 7F.

Figure 4:
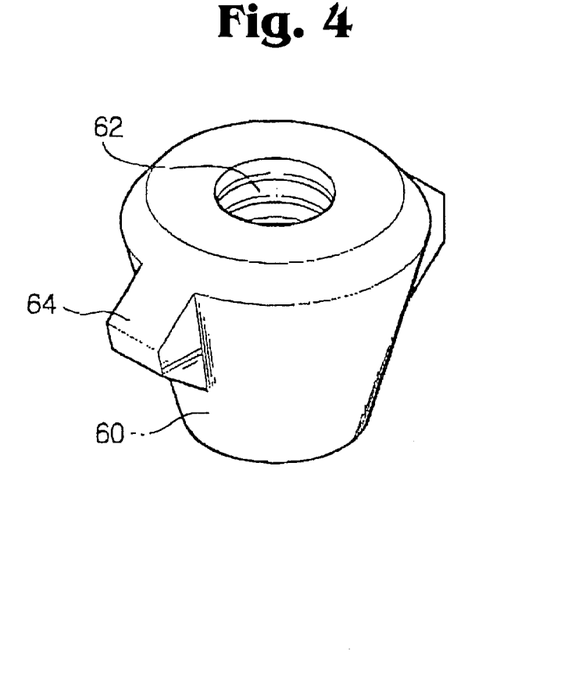
FIG. 4 is a perspective view of a nut according to an embodiment of the present invention.
Figure 5:
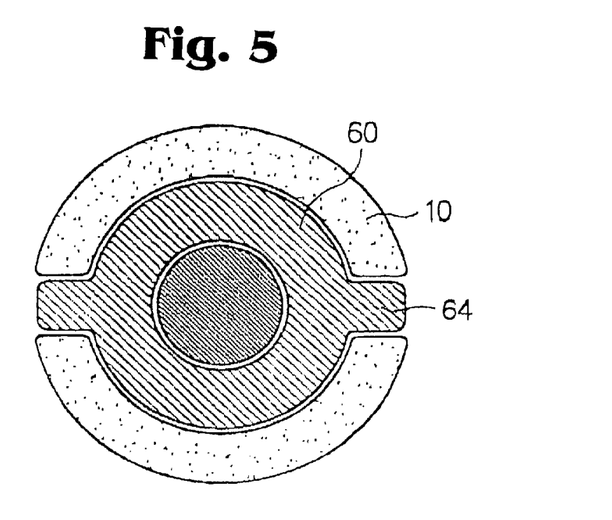
FIG. 5 is a cross-sectional view taken along a line VI—VI in FIG. 2.

And, a nut 60 is screwed on the body portion of the screw 30 which is positioned in the nut receiving portion 19. Referring to FIG. 4, the nut 60 has a shape which its outside diameter is gradually reduced from an upper end toward a lower end thereof. A through hole 62 is formed in the nut 60. Further, on both opposite outer sides of the nut 60, there are provides guiding protrusions 64.

The inside wall of the nut receiving portion 19 entirely has a parabola shape, in which an inside diameter is gradually reduced from an upper end of the nut receiving portion 19 corresponding to the point A. Continuously, the inside wall of the nut receiving portion 19 is firstly bent at a point C corresponding to the point B so that the reducing rate of the inside diameter is slowed. Then, the inside wall of the nut receiving portion 19 is secondly bent at a point D so that the inside diameter of the nut receiving portion 19 is increased. This shape of the inside wall of the nut receiving portion 19 is an example. If the lower body of the fixture body 10 can be expanded by the nut 60 as will be described below, the shape of the inside wall of the nut receiving portion 19 may be varied into other forms.

According to the present invention, the fixture body 10 is formed with at least one slot 14 which is extended from the point B to the lower end of the fixture body 10. In this embodiment, there are provided two slots 14 opposite to each other as shown in FIG. 1 (the opposite slot is not shown). The slot has a width in which the guiding protrusion 64 can be fitted and slid. Further, the number of the slots 14 is provided responding to the number of the guiding protrusions which are formed on the nut 60. In case that the thickness of the fixture body 10 is constant as shown in FIGS. 6A to 6C, there are provided two to four slots 14 in each case so that the guiding protrusions are fitted in each slot 14. In case that the thickness of the fixture body 10 is different according to a position as shown in FIGS. 6D and 6E, a guiding groove 66 is formed in the nut 60, and a thicker portion 10' of the fixture body 10 is inserted into the guiding groove 66 of the nut 60.

Meanwhile, on a lower portion of the abutment 40, there is formed a male screw 42 so as to be engaged with the female screw 22 formed on the inside wall of the abutment receiving portion 18.

The cap 50 is screwed on the lower end of the fixture body 10. The cap 50 is a hemisphere shape having a receiving groove 52, as shown in FIGS. 1 and 2. On the receiving groove 52 of the cap 50, there is formed a thread 54 from its upper edge.

Hereinafter, an operation of the aforementioned implant will be described.

If a tooth is extracted and the socket is formed, a proper implant fixture 100, which is adapted to the form and size of the socket, is selected. At this time, the screw 30 is inserted into the implant fixture 100 and engaged with the nut 60. The cap 50 is coupled to the lower end of the implant fixture 100.

After the cap 50 is removed, the fixture body 10 is inserted into the socket. At this time, since the fixture body 10 is formed into a stepped form, the fixture body 10 is fixedly fitted into the socket.

Then, if the screw 30 is rotated by a desire instrument, the nut 60 is moved downward, since guiding protrusion 64 of the nut 60 is slidably fitted in the slot 14. As described above, in this embodiment in FIGS. 2, 4 and 6A, there are provided two guiding protrusions 64 and two slots 64 corresponding to the guiding protrusions 64. However, although there are provided one slot 14 and one guiding protrusion 64, a sufficient effect can be obtained.

If the nut 60 arrives at the point C, the rest portions of the nut 60 except the guiding protrusion 64 is contacted with the inside wall of the fixture body 10. As described above, the reducing rate of the inside diameter is slowed at the point C. But since the inside diameter is continuously reduced, the inside wall of the fixture body 10 is pushed outward by the nut 60, whereby the fixture body 10 becomes wider after the point C. The expanding rate of the fixture body 10 can be regulated by properly varying the shape of the inside wall of the fixture body 10.

If the fixture body 10 is wider outward by the nut 60, the fixture body 10 is tightly contacted with the inside wall of the socket, since the screw threads 12 are formed on the outer face of the fixture body 10. Moreover, since the screw threads 12 respectively have a sharp end, the fixture body 10 can be fixedly contacted with the inside wall of the socket. Referring to FIG. 3, the nut 60 is moved to the point D, whereby the fixture body 10 is completely contacted with the inside wall of the socket. In this situation, the fixture body 10 is completely fixed to the socket, thereby being prevented from shaking.

Since the cap 50 is removed from the lower end of the fixture body 10, the lower end of the fixture body 10 is expanded outward. In other embodiment, in case that the fixture body 10 is inserted in the socket without removing the cap 50, since the lower end of the fixture body 10 is not expanded by the cap 50 and stably positioned at a bottom face, there is an advantage that the fixture body 10 is not moved due to the expansion of the fixture body 10.

Once the fixture body 10 is fixed to the socket, the screw 30 is not rotated any more. Further, since the ring-shaped protrusion 16 of the partition wall 15 is fitted to the groove 36 of the screw 30, saliva is prevented from being permeated into the nut receiving portion 19 of the fixture body 10, thereby being prevented from being infected with a germ contained in the saliva.

Sequentially, the abutment 40 is inserted into the neck portion 20 of the implant fixture 100. At this time, the shape of the abutment 40 is properly selected into a linear type or an angled type according to the situation. According to the embodiment, the abutment 40 is screwed to the neck portion 20 of the fixture body 10. If necessary, the abutment 40 is attached to the fixture body 10 by an adhesive.

Figure 8:
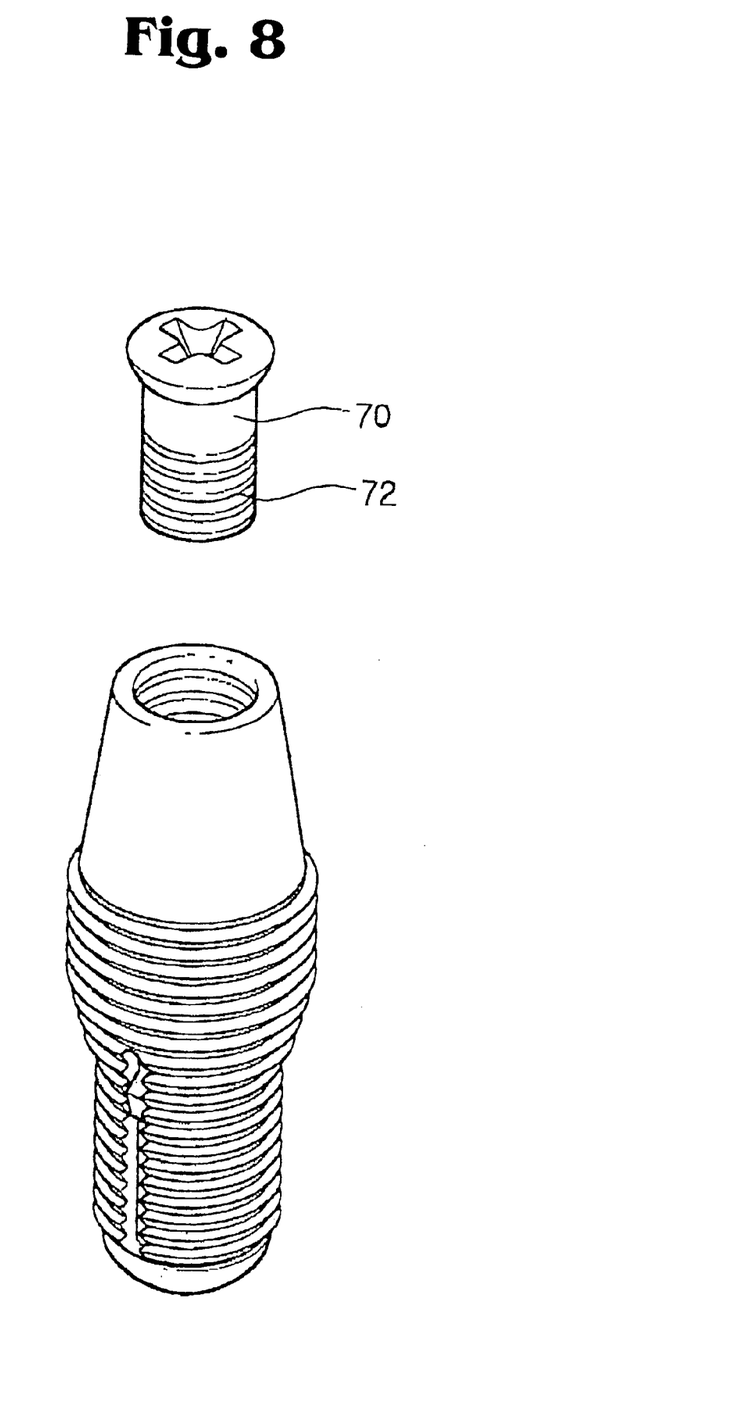
FIG. 8 is an exploded perspective view of a built-in type implant according to other embodiment of the present invention.

FIG. 8 is a perspective view of a built-in type implant 200 according to other embodiment of the present invention.

The structure of the built-in type implant 200 has a similar to that of the implant 100 in FIG. 1. In this embodiment, the built-in type implant 200 comprises a fixture body 10 integrally formed with the abutment 40. Therefore, the neck portion 20 of the implant 100 is not formed. On an inside wall of the abutment 40 of the built-in type implant 200, there is formed a female screw (not shown). A cover 70 formed with a male screw 72 on an outer face thereof is screwed to the abutment 40. That is, after the fixture body 10 is fixed to the socket, the cover 70 is screwed to the abutment 40. Therefore, the operation is very simple.

As described above, according to the present invention, after a tooth is extracted, the fixture body is immediately inserted into the socket. And the lower end of the fixture body is expanded so as to be fixedly contacted with the inside wall of the socket. Then, the abutment or cover is coupled to the fixture body, whereby the operation time is remarkably reduced as well as the operation is simple. Further, since the number of the operation times can be reduced to once, thereby reducing a patient's pain and financial charge.

In addition, since the groove of the screw is sealingly contacted with the ring-shaped protrusion, although the salvia is permeated between the abutment and fixture body or the cover and fixture body, the saliva is prevented from being permeated into the nut receiving portion of the fixture body, thereby being prevented from being infected with a germ contained in the saliva.

Further, since the shape of the implant fixture is designed to be similar to a tooth or the cross section of the fixture body is formed into various shapes, e.g., a circle, an ellipse, an triangle, a trapezoid, etc., although the socket and jawbone is small and narrow, the operation efficient is improved.

It will be apparent to those skilled in the art that various modifications and variations of the present invention can be made without departing from the spirit or scope of the invention. Thus, it is intended that the present invention cover the modifications and variations of this invention provided they come within the scope of the appended claims and their equivalents.

What is claimed is:

1. An implant having a fixture inserted into a socket and an abutment coupled to an upper portion of said fixture, comprising:

said fixture including a hollow body, a plurality of screw threads formed along a circumferential outer surface of said hallow body, and a partition wall having a through hole, said partition wall integrally formed in an inside wall of said hollow body and dividing an inner space of said hollow body into an upper abutment receiving portion and a lower nut receiving portion formed with at least one slot extended from a lower end of said hollow body to a first position, a screw having a head portion resting against said partition wall and disposed in said abutment receiving portion and a body portion inserted into said through hole and extended to a lower portion of said nut receiving portion, a nut fitted to said body potion of said screw and moved upward and downward in said nut receiving portion by the rotation of said screw;

said nut receiving portion formed so that said hollow body is outwardly expanded when said nut is moved to said first position; and a protrusion formed on an upper portion of said partition wall and disposed in said abutment receiving portion, said screw having a groove corresponding to said protrusion.

2. The implant of claim 1, wherein the nut comprises a nut body having a shape corresponding to said socket, a second through hole formed inside said nut body, and a guiding body outwardly projected from said nut body and inserted into said slot, said nut body having a second shape corresponding to said inside wall of said hollow body.

3. The implant of claim 1, with said hollow body integrally formed with a neck portion on an upper portion of said hollow body and formed with a thread to coupled to said abutment.

4. The implant of claim 3, wherein said abutment is a linear type.

5. The implant of claim 3, wherein said abutment is an angled type.

6. The implant of claim 1, wherein the abutment is integrally formed with the fixture body.

7. The implant of claim 6, wherein said abutment is formed with a thread at an inside wall.

8. The implant of claim 1, with said hollow body having at least two slots and divided by said slots into a plurality of parts, said nut having at least two guiding grooves corresponding to respective slots.

9. The implant of claim 1, further comprising a cap coupled to said lower end of said hollow body.

10. The implant of claim 9, said cap having hemisphere shape, a receiving groove for receiving said lower end of said hollow body, and a thread formed on an inside wall of said receiving groove.

11. An implant having a fixture inserted into a socket and an abutment coupled to an upper portion of said fixture, comprising:

said fixture including a hollow body, a screw thread formed along a circumferential outer surface of said hallow body, and a partition wall having a through hole, said partition wall integrally formed in an inside wall of said hollow body and dividing an inner space of said hollow body into an upper abutment receiving portion and a lower nut receiving portion formed with at least one slot extended from a lower end of said hollow body to a first position, a screw having a head portion resting against said partition wall and disposed in said abutment receiving portion and a body portion inserted into said through hole and extended to a lower portion of said nut receiving portion, a nut fitted to said body potion of said screw and moved upward and downward in said nut receiving portion by the rotation of said screw;

said nut receiving portion formed so that said hollow body is outwardly expanded when said nut is moved to said first position;

a protrusion formed on an upper portion of said partition and disposed in said abutment receiving portion, said screw having a groove corresponding to said protrusion; and a cap coupled to said lower end of said hollow body.

12. The implant of claim 11, wherein the cap has a hemisphere shape, a receiving groove formed inside said cap for receiving said lower end of said hollow body, and a thread formed on an inside wall of said receiving groove.

13. The implant of claim 11, wherein the nut comprises a nut body having a shape corresponding to said socket, a second through hole formed inside said nut body, and a guiding body outwardly projected from said nut body and inserted into said slot, said body having a shape corresponding to said inside wall of said hollow body.

14. An implant having a fixture inserted into a socket and an abutment coupled to an upper portion of said fixture, comprising:

said fixture including a hollow body, a plurality of screw threads formed along a circumferential outer surface of said hollow body, and a partition wall formed with a through hole, said partition wall integrally formed in an inside wall and diving an inner space of said hollow body into an upper abutment receiving portion and a lower nut receiving portion, formed with at least one slot extended from a lower end of said hollow body to a first position, a screw having a head portion resting against said the partition wall and disposed in said abutment receiving portion and a body portion inserted into said through hole and extended to a lower portion of said nut receiving portion, a nut having a nut body and a guiding protrusion, said nut having a shape corresponding to said socket and having a through hole receiving said body portion of said screw, said guiding protrusion being outwardly projected from said nut body and being inserted into said slot, said nut moved upward and downward by a rotation of said screw; and an inside wall of said nut receiving portion being a parabola shape having a first position as a peak point, wherein said hollow body being outwardly expanded when said nut is moved from an upper end of said nut receiving portion to said first position.

15. The implant of claim 14, further comprising a cap coupled to said lower end of said hollow body, said cap having a hemisphere shape and a receiving groove for receiving said lower end of said hollow body, said cap having a thread formed on an inside wall of said receiving groove.

16. The implant of claim 14, with said hollow body have an expanding portion being varied according to said parabola shape of said nut receiving portion.

17. The implant of claim 14, said partition will having a protrusion formed on an upper portion of said partition wall and disposed in said abutnent receiving portion, said screw having a groove corresponding to said protrusion wall.

18. The implant of claim 14, wherein with said hollow body formed with a thread coupled to said abutment.

19. The implant of claim 14, with said hollow body having at least two slots and divided by said slots into a plurality of parts, said nut having at least two guiding grooves corresponding to respective slots.

* * * * *